(12) United States Patent
Fuji et al.

(10) Patent No.: US 10,370,632 B2
(45) Date of Patent: Aug. 6, 2019

(54) FACILITY FOR CULTURING PLURIPOTENT STEM CELLS

(71) Applicants: Tokyo Electron Limited, Tokyo (JP); Kajima Corporation, Tokyo (JP)

(72) Inventors: Toshimitsu Fuji, Tokyo (JP); Shigenori Ozaki, Tokyo (JP); Yoshio Kinoshita, Tokyo (JP); Hajime Fujinaga, Tokyo (JP); Ryoji Shiina, Tokyo (JP); Atsushi Nishida, Tokyo (JP)

(73) Assignee: Kajima Corporation, Tokyo (JP)

( * ) Notice: Subject to any disclaimer, the term of this patent is extended or adjusted under 35 U.S.C. 154(b) by 231 days.

(21) Appl. No.: 15/035,879

(22) PCT Filed: Jul. 11, 2014

(86) PCT No.: PCT/JP2014/068560
§ 371 (c)(1),
(2) Date: May 11, 2016

(87) PCT Pub. No.: WO2015/072177
PCT Pub. Date: May 21, 2015

(65) Prior Publication Data
US 2016/0272929 A1 Sep. 22, 2016

(30) Foreign Application Priority Data
Nov. 12, 2013 (JP) ................. 2013-233635

(51) Int. Cl.
| | |
|---|---|
| C12M 1/00 | (2006.01) |
| C12M 1/12 | (2006.01) |
| C12M 3/00 | (2006.01) |
| C12M 1/34 | (2006.01) |
| C12N 5/074 | (2010.01) |

(52) U.S. Cl.
CPC ............ *C12M 23/58* (2013.01); *C12M 21/08* (2013.01); *C12M 37/00* (2013.01); *C12M 41/46* (2013.01); *C12N 5/0607* (2013.01)

(58) Field of Classification Search
CPC ...... C12M 23/58; C12M 21/08; C12M 37/00; C12M 41/46; C12N 5/0607
See application file for complete search history.

(56) References Cited

U.S. PATENT DOCUMENTS

2007/0026032 A1 2/2007 Kantrowitz

FOREIGN PATENT DOCUMENTS

| EP | 2098111 A1 * | 9/2009 | ............... A01G 9/24 |
|---|---|---|---|
| JP | 2004-321111 A | 11/2004 | |
| JP | 2006-094754 | 4/2006 | |
| JP | 4200444 B2 | 10/2008 | |
| JP | 2009-011930 A | 1/2009 | |
| JP | 2009-219415 | 10/2009 | |
| JP | 2009219382 | 10/2009 | |
| JP | 2010-233478 | 10/2010 | |
| JP | 2010284167 | 12/2010 | |
| JP | 4803196 B2 | 10/2011 | |
| JP | 5034043 B1 | 9/2012 | |
| JP | 2013-085528 | 5/2013 | |

OTHER PUBLICATIONS

Takahashi et al., "Programs of Cell Processing Centers for Regenerative Medicine and Bio-safety Facilities for Handling Bacteria and Viruses", Hitachi Review, vol. 89, No. 5, May 2007, pp. 46-51. (Year: 2007).*
Lyons et al. (2007). Setting up a facility for human embryonic stem cell research. Human Stem Cell Manual: A Laboratory Guide. First edition. New York, Elsevier, pp. 389-413. (Year: 2007).*
International Preliminary Report Chapter 1 dated Oct. 14, 2014 for International Application No. PCT/JP2014/068560, seven (7) pages.
Minoru Takahashi et al., "Programs of Cell Processing Centers for Regenerative Medicine and Bio-safety Facilities for Handling Bacteria and Viruses", Hitachi Review, vol. 89, No. 5, May 2007, pp. 46-51.
Ministry of Economy, Trade and Industry of Japan, "Development Guideline 2009—Medical Regeneration Field—Design Guideline for Human Cell Culturing and Processing Apparatus (Revision)", Feb. 2010, pp. 1-14.
International Preliminary Report Chapter 2 dated Feb. 24, 2015 for International Application No. PCT/JP2014/068560, seven (7) pages.
International Preliminary Report Chapter 2 dated Mar. 30, 2016 for International Application No. PCT/JP2014/068560, four (4) pages.
Abou-El-Enein et al., "Good Manufacturing Practices (GMP) manufacturing of advanced therapy medicinal products: a novel tailored model for optimizing performance and estimating costs", Cytotherapy, International Society for Cellular Therapy, 2013; 15, 362-383.

(Continued)

*Primary Examiner* — Titilayo Moloye
(74) *Attorney, Agent, or Firm* — Iandiorio Teska & Coleman, LLP

(57) ABSTRACT

In order to culture the pluripotent stem cell which can be variously differentiated, while preventing the cross contamination between the different cells and securing the safety of the products; extending a main transport path 31 outwardly from a stem cell conditioning area 20, the stem cell conditioning area 20 including a treatment room 21 for inducing pluripotent stem cell from a somatic cell or an egg cell, or a treatment room 21 for receiving and conditioning pluripotent stem cell induced in other facilities; branching at least one branched transport path 32 from the main transport path 31; and arranging along each branched transport path 32, a cell culture area 40 including culture rooms 41 to 44 for culturing the stem cell and an analysis room 45 for analyzing the cultured cell, respectively. Preferably, the stem cell conditioning area 20, the cell culture area 40 and a transport area 30 including the main transport path 31 and the branched transport path 32 are provided with respective operator gates 22, (47+48), 33 individually, so as to prohibit coming and going of operator among the areas 20, 40, 30.

9 Claims, 6 Drawing Sheets

(56) References Cited

OTHER PUBLICATIONS

Lai et al., "Reconstitution of Marrow-Derived Extracellular Matrix Ex Vivo: A Robust Culture System for Expanding Large-Scale Highly Functional Human Mesenchymal Stem Cells", Stem Cells and Development, vol. 19, No. 7, 2010, pp. 1095-1107.
Supplementary European Search Report dated Oct. 20, 2016 and 94 (3) Communication dated Oct. 22, 2016 (ten (10) total pages).

* cited by examiner

[FIG.1]
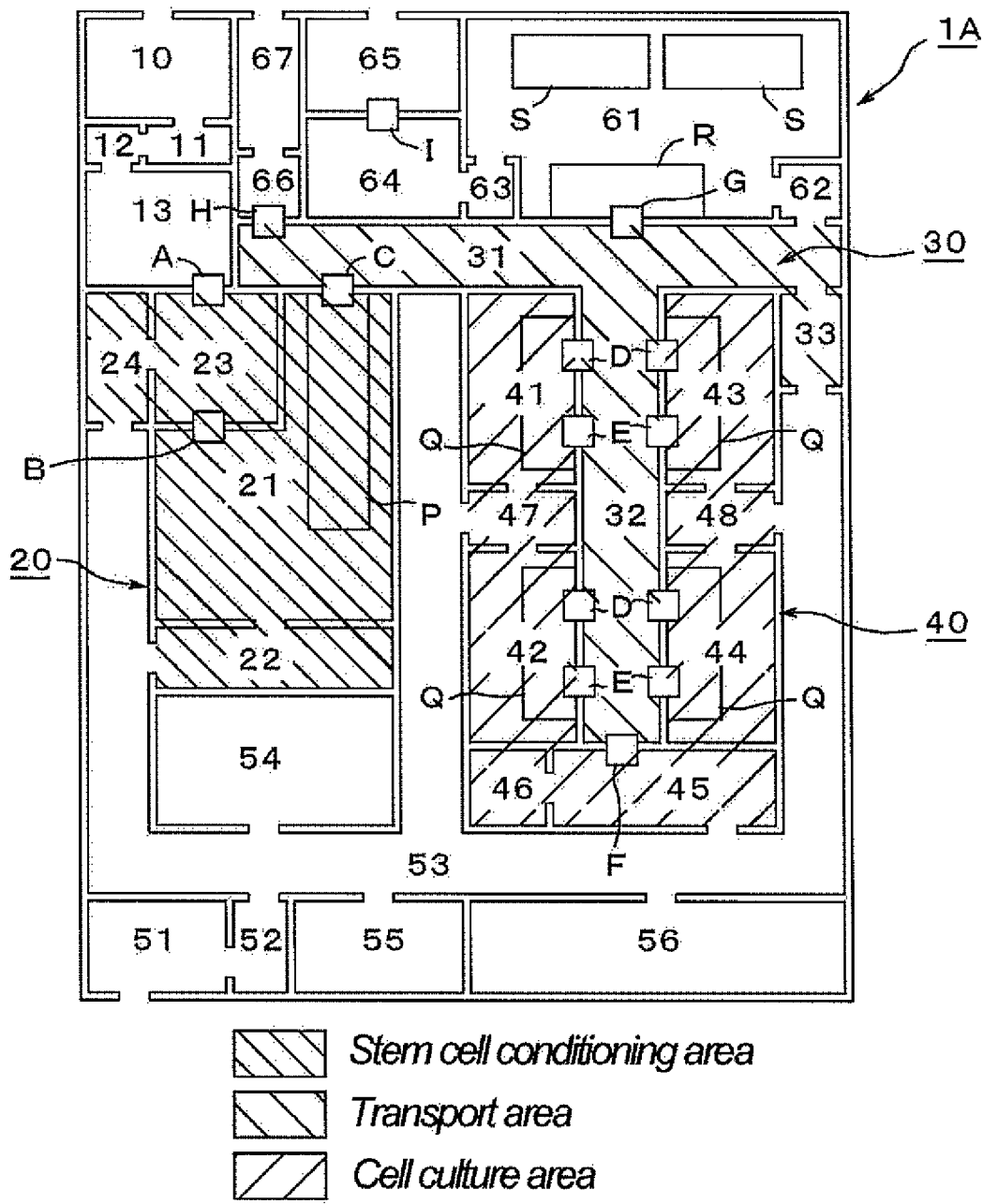

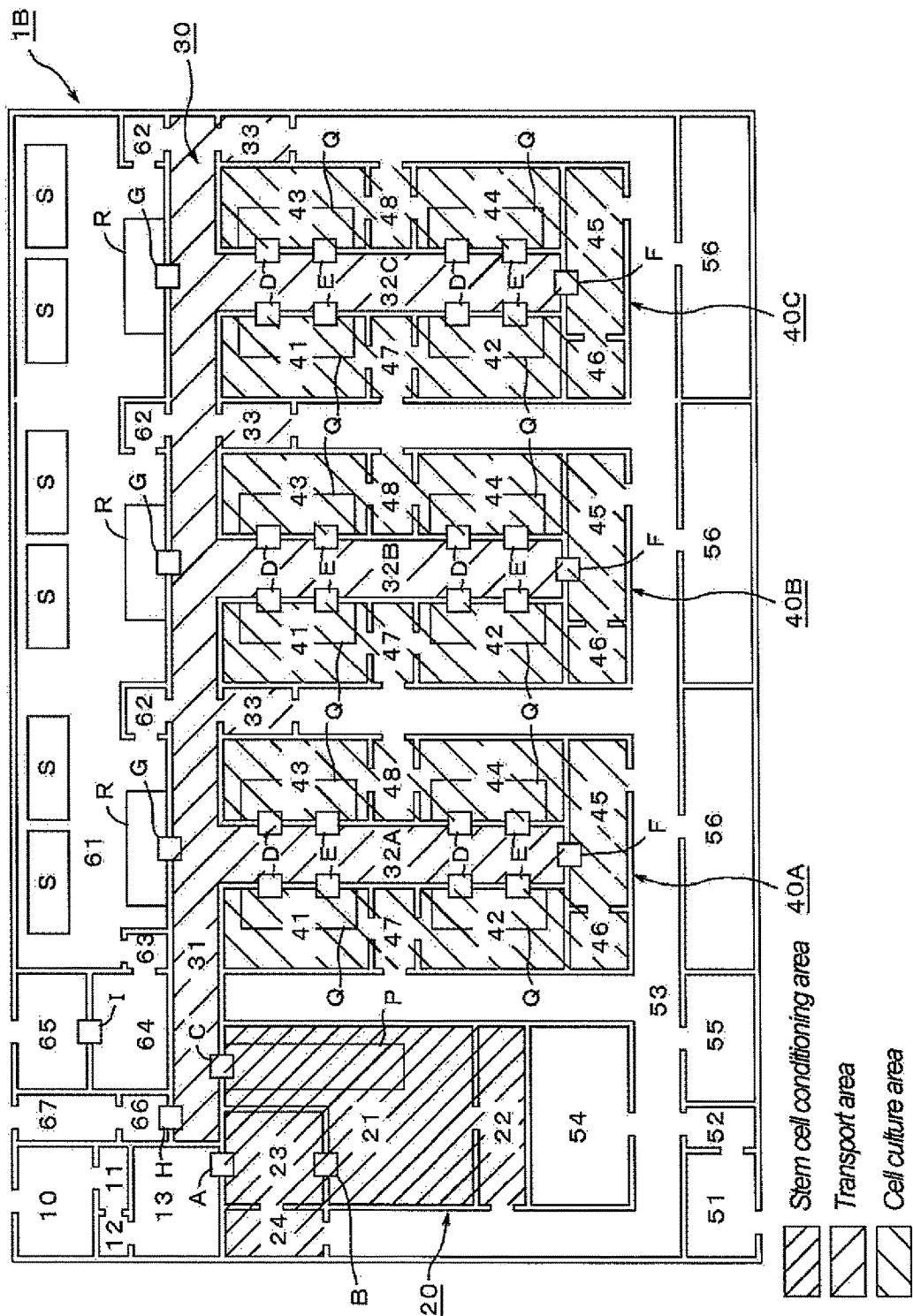

[FIG.3]
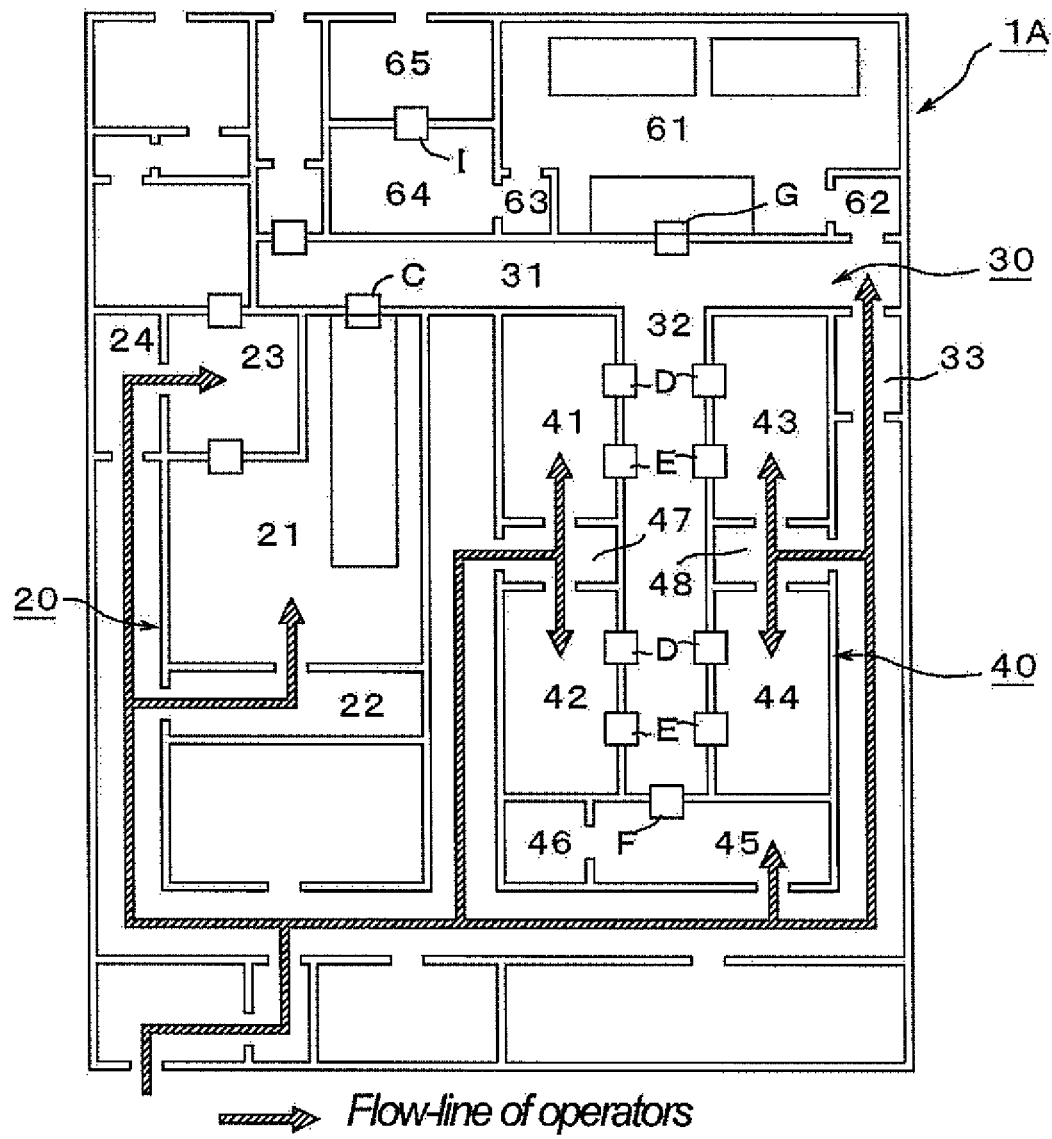
⇒ *Flow-line of operators*

[FIG.4]
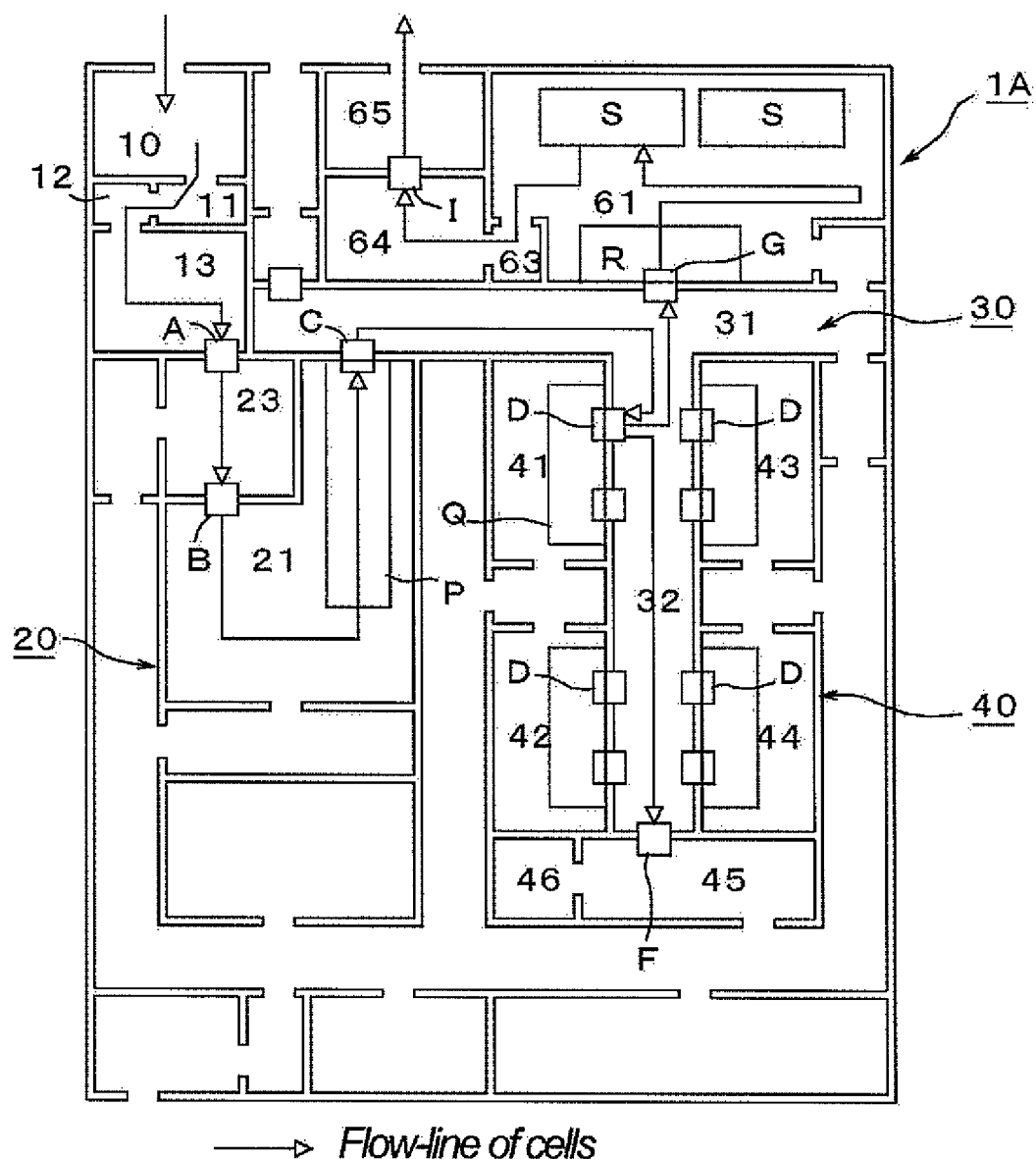
→ Flow-line of cells

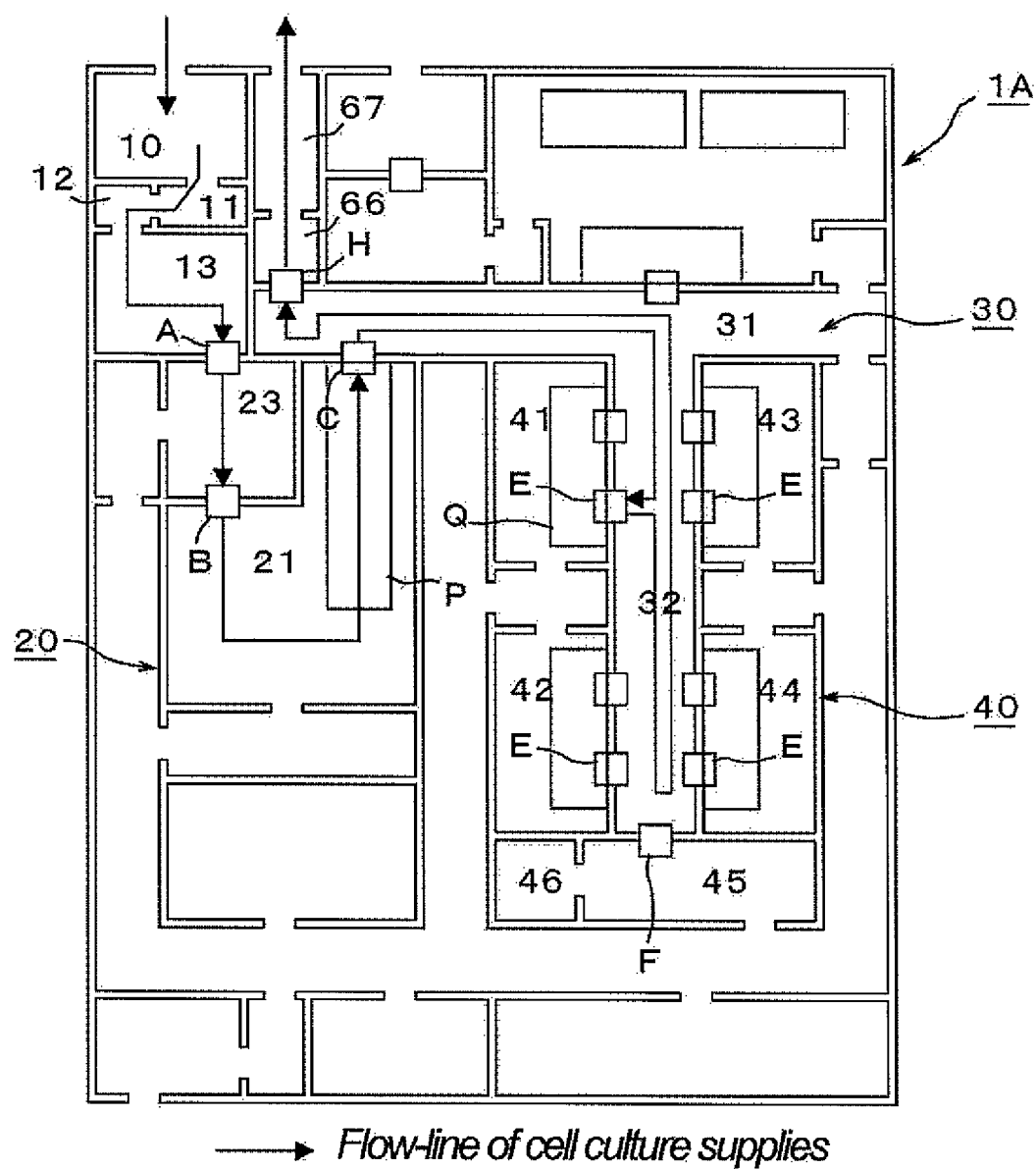
[FIG.5]
→ Flow-line of cell culture supplies

[FIG.6]
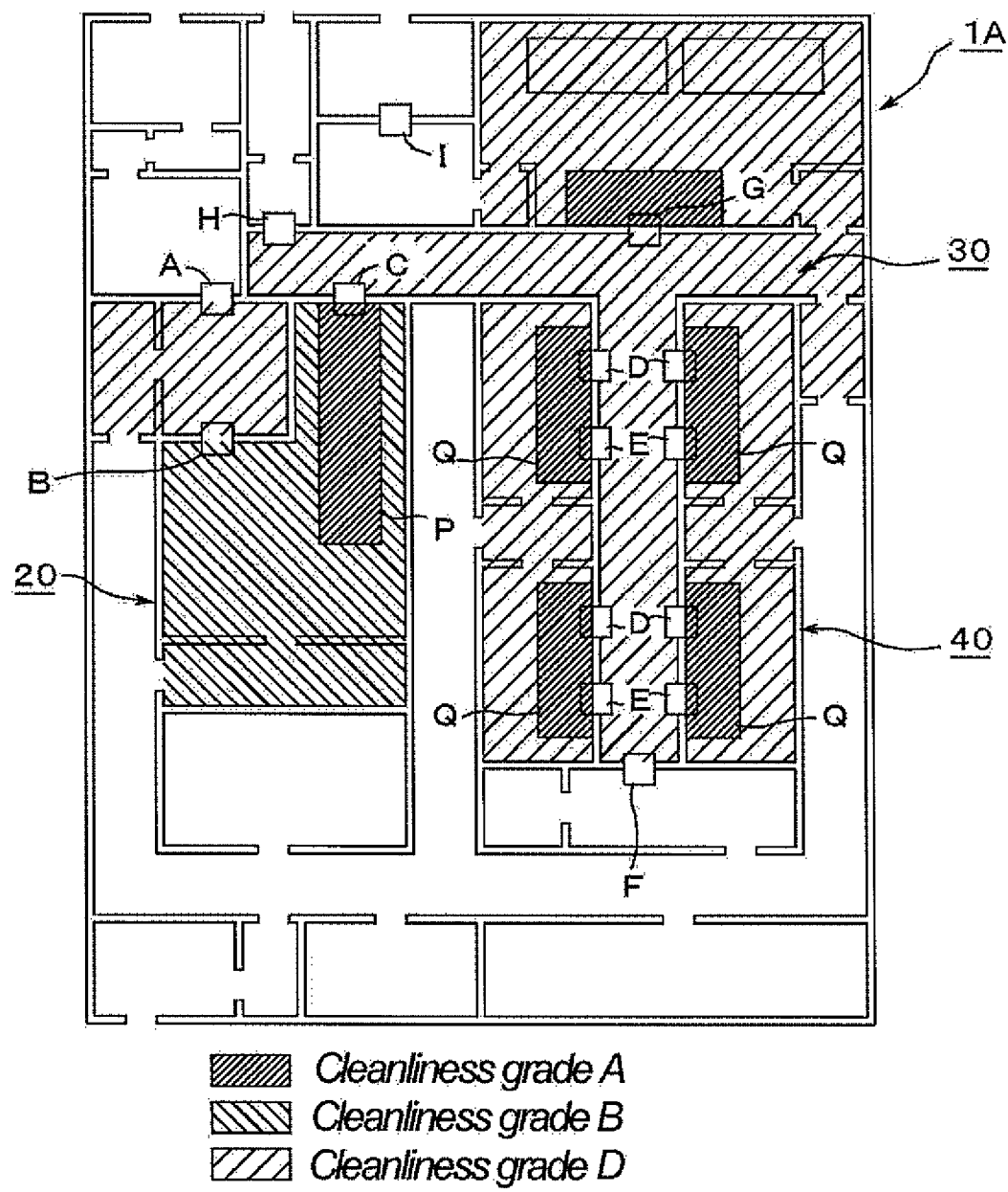

FACILITY FOR CULTURING PLURIPOTENT STEM CELLS

TECHNICAL FIELD

The present invention relates to a method for culturing pluripotent stem cell, and a facility therefor. More particularly, the present invention relates to a method for culturing pluripotent stem cell which can be differentiated into various biotissue cells, and a facility therefor.

BACKGROUND ART

In recent years, ES cell (Embryonic Stem cell) and iPS cell (induced Pluripotent Stem cell) which have ability of differentiation into various tissue cells of human body (hereinafter, referred to as "pluripotency") were discovered, and research and development have been carried out on a technology for putting such ES cell and iPS cell to practical use in drug design field, medical transplantation field, etc. ES cell and iPS cell (hereinafter, collectively referred to as "the pluripotent stem cell") are a type of cell that can be artificially established from an egg cell or a somatic cell, and have ability to differentiate ex vivo into various tissue cells and to self-renew infinitely, i.e. to be grown and divided into two cells, one of which is a differentiated cell and another is a cell of the same type as before.

In the drug design field, the pluripotent stem cell is induced and differentiated from a human somatic cell into a hepatic cell or a cardiac muscle cell, for example, in order to evaluate hepato-toxicity or cardio-toxicity of candidate drug compounds. In the medical transplantation field, the pluripotent stem cell is induced and differentiated from a human somatic cell into a retina cell, a cornea cell, a nerve cell, a dopaminergic cell, an insulin-secreting cell, a cardiac muscle cell, a hepatic cell, etc., in order to supply a source for cell transplantation therapy. Particularly, iPS cell can be induced from an individual somatic cell of any person, whose personality has been found, by a gene-recombination operation, and hence is expected to supply the source of transplantation therapy using autologous iPS cell, i.e. iPS cell established from a somatic cell of a patient who is going to have the transplantation therapy, which will eliminate or reduce the need for immunosuppressive drug owing to prevention of transplant rejection.

In order to put the drug design and the transplantation therapy with the pluripotent stem cell to practical use, there is a need for a cell culture facility in which the pluripotent stem cell can be mass-produced or mass-cultured as differentiating into various tissue cells or without differentiation. In the conventional cell culture facility, stepwise cleanliness control zones are formed, and a cell culture room is arranged in a sterile control zone (clean-room) whose pressure difference is controlled to the surroundings, for culturing cells while securing sterility of products. In order to effectively culture a great amount of cells necessary for the medical transplantation therapy etc., the facility is proposed that a plurality of cell culture rooms are arranged in a sterile control zone (refer to Patent Document Nos 1 to 3). It is also possible to culture a great amount of cells automatically, for example, by arranging an automatic cell culturing apparatus in each of the cell culture rooms in the facility.

Furthermore, when supplying a cell sheet for heart transplantation therapy using the pluripotent stem cell, for example, it is necessary to combine more than one culturing steps, such as a step of growing the undifferentiated pluripotent stem cell, a step of differentiating the stem cell into a particular tissue cell, e.g. a muscle myoblast cell or a cardiac muscle cell, a step of growing the differentiated pluripotent stem cell to prepare a monolayer-cell sheet, a step of stacking a plurality of the cell sheets, etc. If respective culturing steps is carried out in a different culture room, a vast sterile control zone is required in the conventional facility, and cleanliness control in the facility is complicated. A system called "isolator" has been developed to solve the problem, with which each culturing step can be carried out in respective sealed spaces in the system (refer to Patent Document Nos 4 and 5). Using the conventional facility (as described in Patent Document Nos 1 to 3) where a plurality of the isolator (as described in Patent Document Nos 4 and 5) are arranged in respective culture rooms, a great amount of pluripotent stem cell can be cultured by carrying out each of the culturing steps in respective sealed spaces in the isolators, while minimizing the sterile control zone in the facility, resulting in simplifying the cleanliness control in the facility and reducing the operator's support which may causes contamination of the products.

PRIOR ART DOCUMENTS

Patent Documents

[Patent Document No. 1]
Japanese Patent No. 4200444 B1
[Patent Document No. 2]
Japanese Patent No. 4803196 B1
[Patent Document No. 3]
Japanese Patent No. 5035043 B1
[Patent Document No. 4]
Japanese Patent Laying-open Publication No. 2004-32.1111 A
[Patent Document No. 5]
Japanese Patent Laying-open Publication No. 2009-011930 A

SUMMARY OF INVENTION

Technical Problem to be Solved

In the conventional cell culture facility disclosed in Patent Document Nos 1 to 3, more than one culture rooms can be arranged in a sterile control zone for culturing great amount of pluripotent stem cells. However, when respective culture rooms is assigned to different culturing steps or different cells, there is a problem that a cross contamination between the culture rooms may occur in the facility. In case more than one culturing steps are combined for culturing the pluripotent stem cell, as described above, and when each of the culturing step is assigned to the different culture rooms, the cross contaminations between the culture rooms need to be effectively prevented for avoiding contact between the different culturing steps. Further, in case the pluripotent stem cell is to be differentiated into various tissue cells, and when each of the differentiated cell is cultured at the different culture rooms, the cross contaminations between the culture rooms need to be prevented for avoiding contact between the varied differentiated cells.

The isolator, disclosed in Patent Document Nos 4 and 5, is a solution to prevent the cross contamination between the different steps for culturing the pluripotent stem cell. However, in case each of the differentiated cell from the pluripotent stem cell is to be cultured respectively, it is necessary to use more than one isolators for culturing respective varied differentiated cells, as a result of which the cross contamination between the isolators need to be effectively prevented for avoiding contact between the varied differentiated cells. There is a need for a technique for culturing the pluripotent stem cell which can be differentiated into various tissue cells in the single facility, while preventing the cross contamination between the different cells and securing the safety of the products.

Accordingly, it is an objective of the present invention to provide a method and a facility for culturing the pluripotent stem cell which can be variously differentiated, while preventing the cross contamination between the different cells and securing the safety of the products.

Solution to Problem

Referring to FIGS. 1 and 2, the first aspect of the present invention provides a method for culturing pluripotent stem cell comprising the steps of:

extending a main transport path 31 outwardly from a stem cell conditioning area 20, the stem cell conditioning area 20 including a treatment room 21 for inducing pluripotent stem cell from a somatic cell or an egg cell, or a treatment room 21 for receiving and conditioning pluripotent stem cell induced in other facilities;

branching at least one branched transport path 32 (e.g. branched transport paths 32A, 32B, 32C in FIG. 2) from the main transport path 31; and arranging, along each branched transport path 32, a cell culture area 40 (e.g. cell culture areas 40A, 40B, 40C in FIG. 2) including culture rooms 41 to 44 for culturing the stem cell and an analysis room 45 for analyzing the cultured cell, respectively.

Referring to FIGS. 1 and 2, the second aspect of the present invention provides a facility for culturing pluripotent stem cell comprising:

a stem cell conditioning area 20 including a treatment room 21 for inducing pluripotent stem cell from a somatic cell or an egg cell, or a treatment room 21 for receiving and conditioning pluripotent stem cell induced in other facilities;

a transport area 30 including a main transport path 31 extending outwardly from the treatment room 21 and at least one branched transport path 32 (e.g. branched transport paths 32A, 32B, 32C in FIG. 2) from the main transport path 31; and a cell culture area 40 (e.g. cell culture areas 40A, 40B, 40C in FIG. 2) including culture rooms 41 to 44 for culturing the stem cell and an analysis room 45 for analyzing the cultured cell, and being arranged along each branched transport path 32 respectively.

Effects of Invention

The present invention can provide a method and a facility for culturing the pluripotent stem cell which can be variously differentiated, while preventing the cross contamination between the different cells and securing the safety of the products.

BRIEF DESCRIPTION OF DRAWINGS

The present invention may be performed in various ways and a specific embodiment will now be described by way of example, with reference to the accompanying drawings, in which:

FIG. 1 depicts an embodiment of the facility for culturing pluripotent stem cell according to the present invention;

FIG. 2 depicts another embodiment of the facility for culturing pluripotent stem cell according to the present invention;

FIG. 3 depicts a schematic view of flow-line of operators in the facility shown in FIG. 1;

FIG. 4 depicts a schematic view of flow-line of cells in the facility shown in FIG. 1;

FIG. 5 depicts a schematic view of flow-line of cell culture supplies in the facility shown in FIG. 1;

FIG. 6 depicts a schematic view of cleanliness control zone in the facility shown in FIG. 1.

DESCRIPTION OF EMBODIMENTS

FIG. 1 shows an embodiment of a cell culture facility 1 according to the present invention, in which the pluripotent stem cell, e.g. iPS cell, are established from a somatic cell of an animal such as human, and then mass-cultured as differentiating into various tissue cells or without differentiation. Hereinafter, the present invention will be described with reference to the embodiment in FIG. 1. However, the applicable pluripotent stem cell for culturing are not limited to iPS cell in the present invention, and the present invention can be applied to ES cell for establishing from an egg cell and for culturing after established. The cell culture facility 1 in FIG. 1 includes three areas, i.e. a stem cell conditioning area 20, a cell culture area 40, and a transport area 30 for connecting between areas 20 and 40.

The transport area 30 in FIG. 1 includes a main transport path 31 extending outwardly from the stem cell conditioning area 20, and a branched transport path 32 from the main transport path 31. However, as shown in FIG. 2, the transport area 30 may have a plurality of branched transport paths 32A, 32B, 32C, and a plurality of cell culture areas 40A, 40B, 40C may be arranged along respective branched transport path 32A, 32B, 32C. In FIGS. 1 and 2, the stem cell conditioning area 20 and the cell culture area 40 are connected two-dimensionally via the transport area 30. However, the stem cell conditioning area 20 and the cell culture area 40 may be connected three-dimensionally in the facility 1, by including a stairway or an elevator as part of the transport area 30. Additionally or alternatively, more than one cell culture areas 40A, 40B, 40C may be connected three-dimensionally in the facility 1, by including a stairway or an elevator as part of the transport area 30.

The stem cell conditioning area 20 in FIGS. 1 and 2 includes a treatment room 21 for inducing and establishing the pluripotent stem cell from the somatic cell, and a decontamination room 23 for decontaminating or sterilizing the somatic cell and cell culture supplies (e.g. culture vessel, culture medium, etc.) brought from the outside of the facility 1. The stem cell conditioning area 20 also includes a locker room 22 (i.e. operator gate) for entrance and exit of operator for the treatment room 21, and a locker room 24 (i.e. operator gate) for entrance and exit of operator for the decontamination room 23. The decontamination room 23 connects with an receipt/inspection room 10 via a pass-box A, which receipt/inspection room 10 leads to outside of the facility 1, and connects with the treatment room 21 via a transfer-opening B (e.g. opening for transferring the cell and the cell culture supplies with decontamination function). The somatic cell and the cell culture supplies are brought from the outside into the decontamination room 23, and then transferred to the treatment room 21 at a controlled high cleanliness, after their surfaces have been decontaminated passage across the decontamination room 23 and the transfer-opening B.

The treatment room 21 in the stem cell conditioning area 20 is provided with a cell treatment unit P (or safety cabinet P) for establishing the pluripotent stem cell (iPS cell) from the somatic cell brought from the outside, for example, by the gene-recombination operation. In FIGS. 1 and 2, the cell treatment unit P may automatically carry out the operation on the cell in sealed space, and may include the isolator in a part of the unit. Furthermore, the cell treatment unit P is connected with the main transport path 31 in the transport area 30 via a transfer-opening C (e.g. opening for transferring the cell and the cell culture supplies, with or without decontamination function), and sends out the established pluripotent stem cell to the transport area 30 via the transfer-opening C, for example, in a form of being contained in the sealed container (refer to the flow-line of cells in FIG. 4). The sealed container may be a container which can be sterilely connected with the cell treatment unit P (or cell treatment unit Q as described below), while maintaining a sterile inside condition where the established pluripotent stem cell are sealed. Furthermore, in addition to the established pluripotent stem cell, the cell treatment unit P may send out the cell culture supplies necessary for culturing the pluripotent stem cell (e.g. culture vessel, culture medium, etc.), if necessary, via the transfer-opening C to the transport area 30, for example, in a form of being contained in the sealed container (refer to the flow-line of cell culture supplies in FIG. 5).

FIG. 6 shows cleanliness control zones in the cell culture facility 1 of FIG. 1. Cleanliness grades A, B, D in FIG. 6 are defined as shown in Table 1 below, respectively. In the stem cell conditioning area 20, the cell treatment unit P in the treatment room 21 deems to have the cleanliness grade A and is surrounded by a treatment room 21 with the grade B, resulting in a stepwise layout. With such stepwise layout of the cleanliness grades, the pluripotent stem cell can be established using an open-system type safety cabinet as the cell treatment unit P, while contamination risk of the established pluripotent stem cells are minimized. Furthermore, by providing the locker room 22 as the operator gate to the treatment room 21 at high cleanliness from the surroundings at lower cleanliness, a risk of contamination arising from the operator can also be prevented (refer to the flow-line of operators in FIG. 3). In FIG. 6, it is preferable to install transfer-openings B, C, D, E, F, G between the zones with the different cleanliness grades respectively, each of which transfer-opening may be a pass-box with decontamination function. However, it should be noted that the decontamination functions are not essential for the transfer-openings C, D, E, F, G. When the sealed container which can be sterilely connected with the cell treatment unit P, Q is used, as described above, transfer-openings C, D, E, F, G without decontamination function may be applied.

TABLE 1

| | | | Maximum permissible particle number (number/m³) | | | |
|---|---|---|---|---|---|---|
| | | | Not in operation | | In Operation | |
| Name | | Cleanliness level of air | ≥0.5 μm | ≥5.0 μm | ≥0.5 μm | ≥5.0 μm |
| Sterile operation zone | Important zone | Grade A (ISO 5) | 3,520 | 20 | 3,520 | 20 |
| | Direct support zone | Grade B (ISO 7) | 3,520 | 29 | 352,000 | 2,900 |
| | Other support zone | Grade C (ISO 8) | 352,000 | 2,900 | 3,520,000 | 29,000 |
| | | Grade D | 3,520,000 | 29,000 | Depends on operation mode | Depends on operation mode |

The cell culture area 40 in FIGS. 1 and 2 includes culture rooms 41 to 44 for receiving and culturing the pluripotent stem cell established in the stem cell conditioning area 20 through the transport area 30, and an analysis room 45 for analyzing the cells cultured in the culture rooms 41 to 44. The cell culture area 40 also includes locker rooms 47, 48 (i.e. operator gate) for entrance and exit of operator for the culture rooms 41 to 44, and an inactivation room 46 for inactivating and discarding a waste produced in the culture rooms 41 to 44 and the analysis room 45 (e.g. cells or culture medium which have been used or analyzed). In FIGS. 1 and 2, the culture rooms 41 to 44 and the analysis room 45 are connected with the inactivation room 46 by adequate pipes (not shown FIGS. 1 and 2), so that the wastes produced by the culture rooms 41 to 44 and the analysis room 45 (e.g. cells and culture medium which are required to be inactivated) are sent to the inactivation room 46 through the pipes and inactivated there, for example, with heat sterilization or chemical sterilization. Inactivated wastes are discharged from the inactivation room 46 to the outside of the facility.

Each culture room 41 to 44 in the cell culture area 40 is provided with a cell treatment unit Q (or safety cabinet Q) which cultures the pluripotent stem cell as differentiating into various tissue cells or without differentiation. In FIGS. 1 and 2, the cell treatment unit Q may automatically culture the cells in sealed space, and may include the isolator in a part of the unit. Typical example of the cell treatment unit Q is an automatic cell culture apparatus as described below. The cell treatment unit Q in FIGS. 1 and 2 are connected with the branched transport path 32 in the transport area 30 via a transfer-opening D (e.g. opening for transferring the cell and the cell culture medium, with or without decontamination function) and a transfer-opening E (e.g. opening for transferring the cell culture supplies, with or without decontamination function). The cell treatment unit Q receives the sealed container storing the pluripotent stem cell with the culture medium via the transfer-opening D from the transport area 30 (refer to the flow-line of cells in FIG. 4), and receives the sealed container storing the cell culture supplies via the transfer-opening E from the transport area 30 (refer to the flow-line of cell culture supplies in FIG. 5). Each culture room 41 to 44 along same branched transport path 32 are designed to culture same pluripotent stem cell (the stem cell undifferentiated or the stem cell differentiated into particular tissue cells) under same culture condition. In FIGS. 1 and 2, each cell culture area 40 includes four culture rooms 41 to 44 along the branched transport path 32, however, the number of the culture rooms in each cell culture area 40 is changeable according to the volume necessary to be cultured, for example.

As shown in FIG. 6, the cell treatment unit Q in each culture room 41 to 44 in the cell culture area 40 deems to have the cleanliness grade A and is surrounded by the culture room 41 to 49 with the grade D, resulting in a stepwise layout. In FIG. 6, the cleanliness grade B zone is omitted in the culture rooms 41 to 44, contrary to the treatment room 21 as described above. In spite of omission of the grade B, contamination risks are minimized in the culture rooms 41 to 44, because the cell treatment unit Q can carry out operations to the cells in the sealed space, such as the operation to differentiate the cells or the operation to grow the cells. However, it is preferable to create such stepwise layout in the culture rooms 41 to 44 that the cell treatment unit Q is surrounded by the grade B zone as in the treatment room 21, especially when the open-system type safety cabinet is used as the cell treatment unit Q in the culture rooms 41 to 44. Furthermore, by providing the locker rooms 47, 48 as the operator gate to the culture rooms 41 to 44 at high cleanliness from the surroundings at lower cleanliness, contamination risks arising from the operator can also be minimized (refer to the flow-line of operators in FIG. 3).

The analysis room 45 in the cell culture area 40 is provided with an analysis apparatus for analyzing the pluripotent stem cell during culture or after the culture in each culture room 41 to 44, or for analyzing the culture medium during culture or after the culture in each culture room 41 to 44, which analysis apparatus receives the cells and the culture medium via the transfer-opening D (and a transfer-opening F as described below) from each culture room 41 to 44 (refer to the flow-line of cells in FIG. 4). The analysis apparatus in the analysis room 45 is variable in accordance with the culture condition in the culture room 41 to 44. For example, when the undifferentiated pluripotent stem cell is cultured in the culture rooms 41 to 44, the cells during culture are analyzed in the analysis room 45 whether the cells are normally grown in the undifferentiated state or not. Alternatively, when the pluripotent stem cell is differentiated into particular tissue cells and cultured in the culture rooms 41 to 44, the cells during culture are analyzed in the analysis room 45 whether the cells are normally grown as the particular tissue cells or not.

Based on a total evaluation of analysis results in the analysis room 45 and analysis results in the cell treatment unit Q as described below, it is determined that the culture in each culture room 41 to 44 has been completed or not. When the culture is normally completed, the pluripotent stem cell is brought out from the cell treatment unit Q in each culture room 41 to 44 to the branched transport path 32 via the transfer-openings D and sent to a storage room 61 described below (refer to the flow-line of cells in FIG. 4). In FIGS. 1 and 2, as the cell culture area 40 includes both the culture rooms 41 to 44 and the analysis room 45, the cell treatment unit Q can share its modules among the culture room 41 to 44, as shown in the flow-lines in FIGS. 4 and 5.

FIG. 4 shows the flow-line of cells in the cell culture facility 1 of FIG. 1, and FIG. 5 shows the flow-line of cell culture supplies in the cell culture facility 1 of FIG. 1. The cells and the cell culture supplies are both brought into an unpacking room 11 in the facility 1 from the outside, for unpacking, through the receipt/inspection room 10 in the facility 1, and then transferred into a supplies storage room 13 via a pass room 12 for temporary storage. The cells and the cell culture supplies in the supplies storage room 13 are brought into the treatment room 21 in the stem cell conditioning area 20 via the pass-box A and the transfer-opening B with decontamination function, and then used for the establishment of the pluripotent stem cell in the cell treatment unit P (or safety cabinet P) in the treatment room 21. As shown white arrows in FIG. 4, the pluripotent stem cell established in the treatment room 21 are sent out via the transfer-opening C to the main transport path 31 in the transport area 30 in a form of being contained in the sealed container. Further, as shown black arrows in FIG. 5, the cell culture supplies necessary for the culture of the pluripotent stem cell (e.g. culture vessel, culture medium, etc.) are sent out via the transfer-opening C to the main transport path 31 in the transport area 30 in a form of being contained in the sealed container.

As shown in FIG. 4, after sent out the pluripotent stem cell from the stem cell conditioning area 20 to the main transport path 31, the pluripotent stem cell in the main transport path 31 are sent into each culture room 41 to 44 in the cell culture area 40 via the branched transport path 32, and introduced into the cell treatment unit Q (or safety cabinet Q) in each culture room 41 to 44 via the transfer-opening D, and then grown within each cell treatment unit Q. Further, as shown in FIG. 5, after sent out the cell culture supplies from the stem cell conditioning area 20 to the main transport path 31, the cell culture supplies in the main transport path 31 are sent into each culture room 41 to 44 in the cell culture area 40 via the branched transport path 32, and then introduced into the cell treatment unit Q (or safety cabinet Q) in each culture room 41 to 44 via the transfer-opening E.

Moreover, as shown in FIG. 4, the pluripotent stem cell cultured in the cell treatment unit Q in each culture room 41 to 44 are brought out, when necessary, from the transfer-opening D in each culture room 41 to 44 in a form of being contained in the sealed container, and then sent to the analysis room 45 via the transfer-opening F (e.g. opening for transferring the cell and the cell culture medium, with or without decontamination function) for analyzing whether the cells are normally grown. When it is determined that the culture has been normally completed based on the analysis results in the analysis room 45, the cultured pluripotent stem cell is brought out from the transfer-opening D in the cell treatment unit Q in each culture room 41 to 44 to the branched transport path 32 in a form of being contained in the sealed container, and then sent into the storage room 61 via the main transport path 31. When abnormal culture has been detected in the analysis room 45, the pluripotent stem cell during culture is sent out from the cell treatment unit Q in each culture room 41 to 44 into the inactivation room 46 for disposal.

In FIGS. 1 and 2, the storage room 61 for storing the cells cultured in each cell culture area 40 is provided along the main transport path 31 in the culture facility 1, which storage room 61 is connected with the main transport path 31 via the transfer-opening G (e.g. opening for transferring the cell, with or without decontamination function). As shown white arrows in FIG. 4, the pluripotent stem cell normally cultured in each culture room 41 to 44 is sent from the branched transport path 32 to the main transport path 31, and then sent into the storage room 61 via the transfer-opening G connected with the main transport path 31. The storage room 61 is provided with a cell treatment unit R (or safety cabinet R) which seals the pluripotent stem cell in an adequate holder (e.g. an ampoule), so that the pluripotent stem cell is sealed within the holder in the cell treatment unit R and then preserved in the storage room 61, for example, within a freezer or other adequate preservation apparatus S. The cell treatment unit R in FIGS. 1 and 2 may automatically seal the pluripotent stem cell within the holder in sealed space, and may include the isolator in a part of the unit. Further, in FIGS. 1 and 2, the storage room 61 leads to a delivery preparation room 65 via a transfer-opening I (e.g. opening for transferring the cell), so that the pluripotent stem cell preserved in the storage room 61 is transferred into the delivery preparation room 65 for delivery, via the transfer-opening I, and through an inspection/packaging room 64 when necessary.

Moreover, in FIGS. 1 and 2, a waste storage room 67 is provided along the main transport path 31 in the culture facility 1, which storage room 67 is connected with the main transport path 31 via a transfer-opening PI (e.g. opening for transferring the waste). The storage room 67 stores wastes produced in each cell culture area 40 except for the waste to be treated in the inactivation room 46. As shown black arrows in FIG. 5, the waste other than the cell and the culture medium produced in each culture room 41 to 44 is brought out to the branched transport path 32 via the transfer-opening E in a form of being contained in the sealed container, when necessary, and then sent into the waste storage room 67 via the transfer-opening H connected with the main transport path 31 and through a pass room 66. The wastes stored in the waste storage room 67 are brought out to the outside of the facility 1 for disposal, when necessary.

As can be seen from the flow-lines in FIGS. 4 and 5, after the establishment of the pluripotent stem cell in the stem cell conditioning area 20, the culture and the analysis of the pluripotent stem cell in each of the cell culture area 40 can be individually performed, i.e. independently performed from each other, along respective branched transport path 32 in the facility 1. In other words, after the pluripotent stem cell is sent from the stem cell conditioning area 20 to more than one branched transport paths 32, the pluripotent stem cell is cultured in each of the culture rooms 41 to 44 along respective branched transport paths 32, and is determined whether normally cultured or not in the analysis room 45 along respective branched transport path 32, and is inactivated in the inactivation room 46 along respective branched transport paths 32 when necessary, so that the culture operation and the analysis operation along respective branched transport path 32 can be completed independently from other branched transport paths. Therefore, a plurality of the pluripotent stem cell can be cultured in respective branched transport path 32 independently from each other, as differentiating into various tissue cells or without differentiation, while preventing the cross contamination from each other and securing the safety of the products.

In FIGS. 1 and 2, there may be a risk to cross the flow-lines in the main transport path 31, one of which is the flow-line of the pluripotent stem cell before culturing from the main transport path 31 to any of the branched transport paths 32, and another is the flow-line of the pluripotent stem cell (or the waste) after culturing from any of the branched transport paths 32 to the main transport path 31. However, this risk of the cross contamination in the transport area 30 will be minimized by transporting the pluripotent stem cell (and the waste) in a form of being contained in the sealed container, as described above.

Preferably, as shown in FIG. 3, the stem cell conditioning area 20, the cell culture area 40 and the transport area 30 are provided with respective operator gates 22, (47+48), 33 individually, so as to prohibit coming and going of operator among the areas 20, 40, 30. In FIG. 3, the operator of the stem cell conditioning area 20 goes inside the facility 1 from the outside through an entrance gate 51 and a locker room 52, and then enters into and exits from the treatment room 21 through a passageway 53 and the locker room 22 (i.e. operator gate). Further, the operator of the cell culture area 40 enters into and exits from each culture room 41 to 44 through the passageway 53 and the locker rooms 47, 48 (i.e. operator gate), after going inside the facility 1 through the entrance gate 51. The operator can enter into and exit from the analysis room 45 in the cell culture area 40 directly via the passageway 53. Moreover, the operator of the transport area 30 enters into and exits from the main transport path 31 via the passageway 53 and a locker room 33 (i.e. operator gate), after entering into the inside of the facility 1 via the entrance gate 51.

As shown in FIG. 3, the operator of the transport area 30 can transport the cells and the cell culture supplies among the stem cell conditioning area 20, the cell culture area 40 and the storage room 61, and coming and going of the operator among the areas 20, 40, 30 are prohibited, so as to prevent cross contamination among the areas 20, 40, 30 by simplifying the flow-line of operators in the facility 1. Alternatively, an automatic transport apparatus may substitute for the transportation by the operator in the transport area 30. The automatic transport apparatus may be arranged to go and return freely between the main transport path 31 and any of the branched transport paths 32 in the transport area 30, and may transport the cells and the cell culture supplies among the stem cell conditioning area 20, the cell culture area 40 and the storage room 61. In case the automatic transport apparatus substitutes for the transportation by the operator, a need for the operator may be newly arisen to enter into the transport area 30 for maintenance. In FIG. 3, cross contamination due to the maintenance operator is effectively prevented, since coming and going of the operator among the areas 20, 40, 30 are prohibited. Further, as the operator gate 47, 48 are arranged between the culture rooms 41, 42, 43, 44, the maintenance of each culture room 41, 42, 43, 44 are performed individually, i.e. independently from each other. The maintenance of the transport area 30 and the culture rooms 41, 42, 43, 44 includes diagnosis and repair of the apparatus, cleaning of the room, sterilization treatment of the apparatus and/or the room, etc.

FIG. 2 shows another embodiment of the present invention, in which the transport area 30 includes the one main transport path 31 and a plurality of branched transport paths 32A, 32B, 32C, and along each branched transport path 32, the cell culture areas 40A, 40B, 40C are arranged respectively for culturing particular pluripotent stem cell (the stem cell undifferentiated or the stem cell differentiated into particular tissue cells) under particular culture condition. For example, along at least one branched transport path (e.g. the branched transport path 32A), the culture area 40A may be arranged for culturing the undifferentiated pluripotent stem cell, and along other branched transport paths (e.g. the branched transport paths 32B, 32C), the culture areas 40B, 40C may be arranged for culturing the differentiated pluripotent stem cell, so that more than on varied pluripotent stem cell can be simultaneously cultured in the facility 1. By arranging specialized cell culture area 40 along each branched transport path 32 for culturing the particular pluripotent stem cell individually, the flow-line of cells and the flow-line of cell culture supplies that extend between the different cell culture areas 40 are eliminated, and cross contamination of the cells and/or the cell culture supplies is effectively prevented by simplifying the flow-line of cells and cell culture supplies.

Alternatively, in FIG. 2, along each branched transport paths 32A, 32B, 32C, the cell culture areas 40 may be arranged respectively for culturing same pluripotent stem cell (the stem cell undifferentiated or the stem cell differentiated into particular tissue cells) under same culture condition. For example, along each branched transport paths 32A, 32B, 32C, same culture areas 40 are arranged respectively for culturing the undifferentiated pluripotent stem cell. In this case, the analysis room 45 may be so arranged as to connect to each branched transport paths 32A, 32B, 32C for analyzing the same cultured cells jointly, because the analysis room 45 is not necessary to be arranged along each branched transport path 32A, 32B, 32C individually, contrary to the analysis room 45 as described above. In other words, the analysis rooms 45 along the branched transport paths 32B, 32C may be omitted in FIG. 2, and the pluripotent stem cell cultured along all the branched transport paths 32A, 32B, 32C may be analyzed jointly in the analysis room 45 along the branched transport path 32A, i.e. the common analysis room connected to all branched transport paths 32A, 32B, 32C. By arranging the common analysis room 45 connected to more than one branched transport paths 32, quality of the pluripotent stem cell may be improved by simplifying the design of the facility 1 while preventing the cross contamination between the cells, and the construction period of the facility 1 may also be reduced.

In FIGS. 1 and 2, the cell treatment unit Q may be an automatic cell culture apparatus comprising a transport module, an incubator module, a culture medium exchange/analysis module, a cell inspection/removal module, a cell seeding/passage module, and the transfer-openings D, E. The transport module is configured to transport a culture vessel to each of other modules. The incubator module is designed to hold a plurality of the culture vessels in it and maintain a temperature of about 37° C. The culture medium exchange/analysis module is configured to inspect and diagnose a culture state by extracting a part of the culture medium from the culture vessel. The cell inspection/removal module is configured to determine and selectively remove defective cells. The cell seeding/passage module is designed to pick up cells during culture from the culture vessel and to seed them to an empty new culture vessel for the next generation. The transfer-opening D is configured to transfer the sealed container loading more than one culture vessels. The transfer-opening E is configured to transfer the cell culture supplies, e.g. the empty culture vessel, a bottle of the culture medium, an injector of the culture medium into the culture vessel, etc. By assembling these modules, the cell treatment unit Q may automatically culture the cells without manual operation of operator.

FIGS. 1 and 2 shows embodiments in which the stem cell conditioning area 20 includes the treatment room 21 for inducing and establishing the pluripotent stem cell from a somatic cell or an egg cell. However, it should be noted that the design of the stem cell conditioning area 20 of the present invention is not limited to FIGS. 1 and 2. In these days, a system called "iPS Cell Bank (iPSC Bank)" or "ES Cell Bank (ESC Bank)" is proposed and under construction, in which the pluripotent stem cell established from a human somatic cell, e.g. each type of Human Leukocyte Antigen (HLA), are previously preserved for supplying in the future when required. The stem cell conditioning area 20 may include the treatment room 21 for receiving and conditioning the pluripotent stem cell induced in such other facilities as the iPSC Bank or the ESC Bank. In other words, the stem cell conditioning area 20 may be designed for receiving the pluripotent stem cell, not only for establishing the pluripotent stem cell. In case the pluripotent stem cell is received in a frozen state, the cells are thawed out before packed in the culture vessel. The culture vessel may be inspected to determine whether the received pluripotent stem cell is in good condition or not, when necessary, by temporary culturing. The culture vessel is then sealed within the sealed container, and transported to the cell culture area 40 via the transport area 30 as described above. The stem cell conditioning area 20 of the present invention may include both the treatment room 21 for receiving and conditioning the pluripotent stem cell and the treatment room 21 for inducing and establishing the pluripotent stem cell.

Furthermore, the stem cell conditioning area 20, the transport area 30, and the cell culture area 40 may include any optional partitions, e.g. door, air partition, etc., when necessary, though such partitions are omitted in FIGS. 1 and 2.

The present invention provides a method and a facility for culturing pluripotent stem cell comprising the steps of:

providing the stem cell conditioning area 20 including a treatment room 21 for inducing pluripotent stem cell from a somatic cell or an egg cell, or a treatment room 21 for receiving and conditioning pluripotent stem cell induced in other facilities, providing the transport area 30 including the main transport path 31 extending outwardly from the treatment room 21, and at least one branched transport path 32 branching from the main transport path 31; and arranging, along each branched transport path 32, a cell culture area 40 including culture rooms 41 to 44 for culturing the stem cell and an analysis room 45 for analyzing the cultured cell, respectively.

And hence, the following effects can be achieved as a result.

(a) As each cell culture area 40 includes the culture rooms 41 to 44 and the analysis room 45, the culture and the analysis in each cell culture area 40 may be performed independently from each other, so that an individual culture module designed for culturing a particular pluripotent stem cell, e.g. the stem cell undifferentiated or the stem cell differentiated into particular tissue cells, may be created in each cell culture area 40.

(b) In case more than one cell culture areas 40 for culturing a particular stem cell are arranged in a single facility 1, each cell culture areas 40 may be arranged along different branched transport path 32, and flow-line of cells and the flow-line of cell culture supplies among different cell culture areas 40 are eliminated, as a result of which cross contamination is effectively prevented by simplifying the flow-line of cells and cell culture supplies.

(c) Further, the stem cell conditioning area 20, the cell culture area 40 and the transport area 30 may be provided with respective operator gates 22, (47+48), 33 individually, so as to prohibit coming and going of operator among the areas 20, 40, 30, as a result of which cross contamination is effectively prevented by simplifying the flow-line of operators.

(d) By increasing the number of the branched transport paths 32 from the main transport path 31, not only two-dimensionally (in planar structure) but also three-dimensionally (in multilayer structure), the number of the cell culture areas 40 and the type of the pluripotent stem cell to be cultured in the facility may be easily increased.

(e) Furthermore, each cell culture area 40 may be a similar design and structure, so that the quality of the cells can be improved by simplifying the design and structure of the facility, which results in reduction of the construction period of the facility, regardless of the number or the type of the pluripotent stem cell to be cultured.

Thus, the object of the present invention, namely to provide a method and a facility for culturing the pluripotent stem cell which can be variously differentiated, while preventing the cross contamination between the different cells and securing the safety of the products, has been fulfilled.

REFERENCE NUMERALS

1 . . . cell culture facility
10 . . . receipt/inspection room
11 . . . unpacking room
12 . . . pass room
13 . . . supplies storage room
20 . . . stem cell conditioning area
21 . . . treatment room
22 . . . operator gate (locker room)
23 . . . decontamination room
24 . . . operator gate (locker room)
30 . . . transport area
31 . . . main transport path
32 . . . branched transport path
33 . . . operator gate (locker room)
40 . . . cell culture area
41, 42, 43, 44 . . . culture room
45 . . . analysis room
46 . . . inactivation room
47, 48 . . . operator gate (locker room)
51 . . . entrance gate for operator
52 . . . locker room
53 . . . passageway
54 . . . shared space
55 . . . shared space
56 . . . machinery room
61 . . . storage room
62 . . . operator gate (airlock)
63 . . . pass room
64 . . . inspection/packaging room
65 . . . delivery preparation room
66 . . . pass room
67 . . . waste storage room
A . . . pass-box
B . . . transfer-opening (opening for transferring the cell and the cell culture supplies, with decontamination function)
C . . . transfer-opening (opening for transferring the cell and the cell culture supplies, with or without decontamination function)
D . . . transfer-opening (opening for transferring the cell and the cell culture medium, with or without decontamination function)
E . . . transfer-opening (opening for transferring the cell culture supplies, with or without decontamination function)
F . . . transfer-opening (opening for transferring the cell and the cell culture medium, with or without decontamination function)
G . . . transfer-opening (opening for transferring the cell, with or without decontamination function)
H . . . transfer-opening (opening for transferring the waste).
I . . . transfer-opening (opening for transfer of the cell)
P, Q, R . . . cell treatment unit or safety cabinet
S . . . storage apparatus

The invention claimed is:

1. A facility for culturing pluripotent stem cell comprising:
a stem cell conditioning area including a treatment room for receiving a somatic cell or an egg cell from outside and inducing pluripotent stem cell from the somatic cell or the egg cell, or a treatment room for receiving and conditioning pluripotent stem cell induced in other facilities from outside;
a transport area including a main transport path extending outwardly from the treatment room and a plurality of branched transport paths from the main transport path; and
a plurality of cell culture areas including a culture room for culturing the stem cell as differentiating into a particular cell or without differentiation and an analysis room for analyzing the cultured cells, and being arranged along each branched transport path respectively,
wherein the treatment room in the stem cell conditioning area is connected with the main transport path via a transfer-opening, and the culture room and the analysis room in each cell culture area are connected with the branched transport path, respectively, via a transfer-opening, and
the stem cell conditioning area, each of the cell culture area, and the transport area are provided with respective operator gates to outside of all areas individually, and no operator gate is provided between the stem cell conditioning area and the transport area, no operator gate is provided between the transport area and each of the cell culture area, and no operator gate is provided between each of the cell culture area.

2. The facility for culturing pluripotent stem cell according to claim 1, wherein a storage room for storing the cells cultured in each cell culture area is provided along the main transport path in the transport area, the storage room being connected with the main transport path via a transfer-opening.

3. The facility for culturing pluripotent stem cell according to claim 2, wherein the storage room leads to a delivery preparation room via a transfer-opening.

4. The facility for culturing pluripotent stem cell according to claim 1, wherein along at least one branched transport path, the culture area is arranged that includes the culture room for culturing the undifferentiated pluripotent stem cell and the analysis room for analyzing it; and along other branched transport path, the culture area is arranged that includes the culture room for culturing a particular cell differentiated from the stem cell and the analysis room for analyzing said particular cell.

5. The facility for culturing pluripotent stem cell according to claim 2, wherein along at least one branched transport path, the culture area is arranged that includes the culture room for culturing the undifferentiated pluripotent stem cell and the analysis room for analyzing it; and along other branched transport path, the culture area is arranged that includes the culture room for culturing a particular cell differentiated from the stem cell and the analysis room for analyzing said particular cell.

6. The facility for culturing pluripotent stem cell according to claim 3, wherein along at least one branched transport path, the culture area is arranged that includes the culture room for culturing the undifferentiated pluripotent stem cell and the analysis room for analyzing it; and along other branched transport path, the culture area is arranged that includes the culture room for culturing a particular cell differentiated from the stem cell and the analysis room for analyzing said particular cell.

7. The facility for culturing pluripotent stem cell according to claim 1, wherein along each branched transport paths, the culture areas are arranged that includes the culture room for culturing the undifferentiated pluripotent stem cell; and connecting to each branched transport paths, the analysis room is arranged for analyzing the cultured cells jointly.

8. The facility for culturing pluripotent stem cell according to claim 2, wherein along each branched transport paths, the culture areas are arranged that includes the culture room for culturing the undifferentiated pluripotent stem cell; and connecting to each branched transport paths, the analysis room is arranged for analyzing the cultured cells jointly.

9. The facility for culturing pluripotent stem cell according to claim 3, wherein along each branched transport paths, the culture areas are arranged that includes the culture room for culturing the undifferentiated pluripotent stem cell; and connecting to each branched transport paths, the analysis room is arranged for analyzing the cultured cells jointly.

* * * * *